United States Patent [19]

Schmalstieg et al.

[11] Patent Number: 5,610,260
[45] Date of Patent: Mar. 11, 1997

[54] POLYISOCYANATE MIXTURES WHICH ARE LIQUID AT GREATER THAN 5° C

[75] Inventors: Lutz Schmalstieg; Josef Pedain; Harald Mertes, all of Köln, Germany

[73] Assignee: Bayer Aktiengesellschaft, Leverkusen, Germany

[21] Appl. No.: 599,640

[22] Filed: Feb. 9, 1996

Related U.S. Application Data

[63] Continuation of Ser. No. 377,873, Jan. 25, 1995, abandoned.

[30] Foreign Application Priority Data

Feb. 3, 1994 [DE] Germany .......................... 44 03 233.1

[51] Int. Cl.$^6$ ................................................ C08G 18/10
[52] U.S. Cl. .................... 528/49; 528/65; 252/182.21; 252/182.22; 560/25
[58] Field of Search ................. 252/182.21, 182.22; 528/49, 65; 560/25

[56] References Cited

U.S. PATENT DOCUMENTS

| | | | |
|---|---|---|---|
| 3,644,457 | 2/1972 | König et al. | 560/351 |
| 4,014,935 | 3/1977 | Ibbotson | 540/202 |
| 4,088,665 | 5/1978 | Findeisen et al. | 560/334 |
| 4,154,752 | 5/1979 | Sundermann et al. | 560/334 |
| 4,738,991 | 4/1988 | Narayan | 521/124 |
| 4,883,909 | 11/1989 | Slack | 560/351 |
| 5,319,053 | 6/1994 | Slack et al. | 528/48 |
| 5,319,054 | 6/1994 | Slack et al. | 528/48 |

FOREIGN PATENT DOCUMENTS

| | | |
|---|---|---|
| 019375 | 11/1980 | European Pat. Off. . |
| 1092007 | 11/1960 | Germany . |
| 1430455 | 1/1973 | United Kingdom . |
| 1369334 | 10/1974 | United Kingdom . |
| 1377676 | 12/1974 | United Kingdom . |
| 2066813 | 7/1981 | United Kingdom . |

*Primary Examiner*—Rachel Gorr
*Attorney, Agent, or Firm*—Joseph C. Gil; Thomas W. Roy

[57] ABSTRACT

The present invention relates to polyisocyanate mixtures which are reaction products of 4,4'-diphenylmethane diisocyanate as the isocyanate component, are liquid at greater than 5° C. and have an NCO content of 14.5 to 24% by weight and an allophanate group content (calculated as $C_2HN_2O_3$, molecular weight = 101) of 7.7 to 14.5% by weight; a process for the production of these polyisocyanate mixtures by reacting 4,4'-diphenylmethane diisocyanate as the exclusive isocyanate component with one or more monohydric alcohols having 4 to 16 carbon atoms at an NCO/OH equivalent ratio of 5:1 to 8.5:1 and at a temperature of up to 160° C. to form urethane groups and during or subsequent to urethane formation, converting the urethane groups to allophanate groups in the presence of a catalyst which promotes allophanate formation; and the use of these polyisocyanate mixtures as the polyisocyanate component in two-component polyurethane coating compositions.

6 Claims, No Drawings

POLYISOCYANATE MIXTURES WHICH ARE LIQUID AT GREATER THAN 5° C

This application is a continuation of application Ser. No. 08/377,873 filed Jan. 25, 1995, now abandoned.

BACKGROUND OF THE INVENTION

1. Field of the Invention

The present invention relates to liquid polyisocyanate mixtures based on 4,4'-diphenylmethane diisocyanate and containing allophanate groups, a process for their production and their use for the production of two-component polyurethane coating compositions.

2. Description of the Prior Art

Two-component polyurethane coating compositions based on diphenyl-methane diisocyanate are known and described, e.g., in "Wagner-Sarx, Lackkunstharze, 5th edition, Carl Hanser Verlag, Munich, For the production of solvent-free two-component polyurethane systems which enable thick coatings to be produced in one operation, liquid polyisocyanate mixtures of the diphenylmethane series are generally used as the polyisocyanate component. These are usually undistilled and therefore strongly colored polyisocyanate mixtures that are obtained in known manner by the phosgenation of aniline/formaldehyde condensates.

For decorative applications, such as floor coatings, it is desirable to use light-colored diphenylmethane diisocyanate mixtures. Such liquid, light-colored polyisocyanates include mixtures of 4,4'-diphenylmethane diisocyanate with greater quantities of 2,4'-diphenylmethane diisocyanate. Mixtures of this type display poor resistance to crystallization at low temperatures, and also the 2,4'-diphenylmethane diisocyanate portion markedly impairs the properties of the coating materials produced therefrom. There is a demand for light-colored, non-crystallizing polyisocyanate mixtures which are based exclusively on 4,4'-diphenylmethane diisocyanate and are suitable for the purpose mentioned.

The production of modified polyisocyanate mixtures based on 4,4'-diphenyl-methane diisocyanate which are liquid at ambient temperature is known. For the production of mixtures of this type, according to DE-PS 1,618,380 for example, 1 mole 4,4'-diphenylmethane diisocyanate is reacted with 0.1 to 0.3 mole tri-1,2-oxypropylene glycol and/or poly-1,2-oxypropylene glycol having a molecular weight of up to 700. According to GB-PS 1,369,334 the modification is performed in two reaction steps and dipropylene glycol or polyoxypropylene glycol having a molecular weight of less than 2000 is used as the modifier.

DE-OS 2,913,126 describes diphenylmethane diisocyanate compositions in which 10 to 35% by weight of the isocyanate groups are reacted with a mixture of at least 3 alkylene glycols, wherein one of these glycols is di-, tri-or polypropylene glycol. In DE-OS 2,404,166 mixtures of polyoxyethylene glycol or polyoxypropylene glycol having an average molecular weight of less than 650 and at least one alkylene glycol having at least 3 C atoms are mentioned as modifiers. DE-OS 2.346,996 relates to diphenylmethane diisocyanate compositions in which 10 to 35 % by weight of the isocyanate groups are reacted with a commercial polyethylene glycol. Finally, according to EP-A 0,341,515, 4,4'-diphenyl-methane diisocyanate is modified with mixtures of aminopolyethers and tripropylene glycol.

All of the polyisocyanate mixtures described in these publications contain incorporated ether structures due to the incorporation of polyether polyols. From an application standpoint this is disadvantageous. Even though the incorporation of these polyols leads to an elasticizing of the finished products which is often undesirable, such polyoxyalkylene oxide units are known to be sensitive to oxidative degradation.

Liquid polyisocyanate mixtures based on 4,4'-diphenylmethane diisocyanate which do not contain any ether structures can be obtained by proportional carbodiimidization of 4,4'-diphenylmethane diisocyanate, as is described for example in DE-PS 1,092,007, DE-OS 2,537,685, U.S. Pat. No. 4,014,935, U.S. Pat. No. 4,088,665 and U.S. Pat. No. 4,154,752. This method also has disadvantages since even though product mixtures which have only a small proportion of carbodiimide structures display a sufficiently low viscosity, they suffer from poor resistance to crystallization, particularly at temperatures below 10° C. Product mixtures which have a larger proportion of carbodiimide structures display satisfactory resistance to crystallization, but have to high a viscosity for many applications (cf. e.g. DE-OS 2,537,685, Examples 1 to 3).

In order to overcome these problems modification with polyalkylene oxide polyols is often undertaken in addition to the carbodiimide modification. However, this results in the disadvantages described.

It is an object of the present invention to provide low-viscosity polyisocyanate mixtures based on 4,4'-diphenylmethane diisocyanate which are non-crystallizing at 5° C. and which do not contain any ether or polyalkylene oxide structures.

This object was achieved with the polyisocyanate mixtures containing allophanate groups described in more detail below.

SUMMARY OF THE INVENTION

The present invention relates to polyisocyanate mixtures which are reaction products of 4,4'-diphenylmethane diisocyanate (as hereinafter defined) as only isocyanate component, are liquid at greater than 5° C. and have A) an NCO content of 14.5 to 24% by weight and B) an allophanate group content (calculated as $C_2HN_2O_3$, molecular weight = 101) of 7.7 to 14.5% by weight.

The present invention also relates to a process for the production of these polyisocyanate mixtures by reacting 4,4'-diphenylmethane diisocyanate (as hereinafter defined) as the exclusive isocyanate component with one or more monohydric alcohols having 4 to 16 carbon atoms at an NCO/OH equivalent ratio of 5:1 to 8.5:1 and at a temperature of up to 160° C. to form urethane groups and during or subsequent to urethane formation, converting the urethane groups to allophanate groups in the presence of a catalyst which promotes allophanate formation.

Finally, the present invention relates to the use of the polyisocyanate mixtures according to the invention as the polyisocyanate component in two-component polyurethane coating compositions.

DETAILED DESCRIPTION OF THE INVENTION

Polyisocyanate mixtures which contain allophanate groups are known and are described for example in U.S. Pat. No. 3,769,318 and GB-PS 994,890. Although 4,4'-diphenylmethane diisocyanate is mentioned as a suitable starting material, it can be stated that no indication can be derived from these publications as to whether and under what conditions liquid, non-crystallizing polyisocyanate mixtures can be produced by the modification of 4,4'-diphenylmethane diisocyanate.

Starting materials for the process according to the invention include "4,4'-diphenylmethane diisocyanate". This term stands for pure 4,4'-diphenylmethane diisocyanate as well as for its mixtures with up to 1,95% by weight of 2,4'-diphenylmethane diisocyanate and/or with up to 0,5 % by weight of 2,2'-diphenylmethane diisocyanate said percentages being based on the total mixture. Preferably the term "4,4'-diphenylmethane diisocyanate" as used hereinbefore and hereinafter stands for a mixture containing at least 98,5% by weight of the 4,4'-isomer in addition to said 2,2'- und 2,4'-isomers. Further starting materials for the process according to the invention include preferably ether group-free alcohols having 4 to 10 carbon atoms, which are liquid at ambient temperature. Mixtures of various alcohols of this type may also be used.

Suitable alcohols include n-butanol, i-butanol, n-pentanol, n-hexanol, 2-ethylhexanol, n-octanol, n-decanol, n-dodecanol or n-hexadecanol. Monohydric alcohols containing ether groups, which may be obtained by the ethoxylation or propoxylation of the preceding alcohols (such as diethylene glycol monobutyl ether), may also be used in principle. However, the use of such ether group-containing monoalcohols is certainly not preferred since an object of the present invention to provide products that do not contain ether oxygen atoms.

The conversion takes place following or during intermediate urethane formation in the presence of catalysts which promote allophanate formation. Suitable catalysts include metal compounds from main groups 3 and 4 (i.e., IIIa and IVa) and subgroups 1, 2, 6, 7 and 8 (i.e., Ib, IIb, VIb, VIIb and VIIIb) of the Periodic Table, which are soluble in the reaction mixture, such as those described in U.S. Pat. No. 3,769.318. Tin(II) octoate or zinc acetylacetonate are preferably used. The catalyst is present in quantities of 20 to 2000 ppm (by weight), preferably 20 to 200 ppm (by weight), based on the weight of the reaction mixture. The presence of compounds having an alkylating effect during the reaction is not necessary, contrary to the recommendation in U.S. Pat. No. 3,769.318. Surprisingly, the polyisocyanate mixtures according to the invention exclusively contain allophanate structures and no urethane, isocyanurate and/or carbodiimide structures. This may be confirmed by $C^{13}$ NMR spectroscopic investigations.

The process according to the invention is carried out at temperatures of up to 160° C. The preferred temperature with respect to the allophanatization reaction is 80°to 120° C. According to a preferred operating method the polyisocyanate mixtures according to the invention are produced in a 2-step process. In the first process step, molten 4,4'-diphenylmethane diisocyanate is prepared and the monoalcohol is added dropwise at a temperature of 40° C. to 80° C., preferably 50° C. to 70° C. Once the calculated NCO content for urethane formation has been reached, the catalyst is added in the second process step and the temperature is subsequently increased to 80° to 160° C., preferably 80° to 120° C. The reaction is terminated once the calculated NCO content for allophanate formation is reached, preferably by adding a catalytic poison.

Suitable catalytic poisons include compounds having an alkylating or acylating effect (such as p-toluenesulphonic acid methyl ester, dimethyl sulphate, benzoyl chloride and isophthalic acid dichloride), which are preferably added in at least equimolar quantities, based on the quantity of catalyst used.

The polyisocyanate mixtures according to the invention are almost colorless, liquid mixtures with surprisingly low viscosities of 200 to 5000 mPa.s (23° C.); the viscosity increases as the quantity of allophanate structures increases. The NCO content of the polyisocyanate mixtures according to the invention is 14.5 to 24% by weight.

The polyisocyanate mixtures according to the invention display excellent resistance to crystallization at low temperatures. Product mixtures with a high proportion of allophanate structures display no crystallization at all, even at temperatures below 0° C.

The polyisocyanate mixtures according to the invention are suitable starting compounds for the production of polyurethane plastics in general, but the mixtures are preferably used for the production of solvent-free polyurethane coating compositions. For the production of such coating compositions the polyisocyanate mixtures according to the invention are combined with solvent-free polyhydroxyl compounds or mixtures of such compounds which are known from polyurethane chemistry. The amounts of the individual components are chosen to provide an NCO/OH equivalent ratio of 0.8:1 to 1.5:1. Suitable polyhydroxyl compounds include polyether, polyester and/or polycarbonate polyols.

Because of the bubble-free cure in a thick coat, the polyisocyanate mixtures according to the invention are preferably combined with castor oil or blends of castor oil with ketone-formaldehyde condensates, polyester polyols and/or polyether polyols.

Transparent, light-colored coatings with high hardness and good abrasion resistance are obtained from these compositions. The hardness of the coatings obtained is greater than the hardness of similar coatings cured with 4,4'-diphenyl-methane diisocyanate. Pigments and other additives (such as fillers, flow control additives, etc.) may be added to the compositions or to one of the starting components.

The coating materials containing the polyisocyanate mixtures according to the invention may be applied to any substrates in one or several coats by known methods such as spraying, brushing, dipping, flow coating or with the aid of rollers or doctor blades. Metal, wood, glass, stone, ceramic materials, concrete, rigid and flexible plastics, textiles, leather or paper are examples of suitable substrates. The substrates may of course be provided with known primers prior to the application of the coating compositions according to the invention.

The following examples serve to explain the invention further. All parts and percentages are based on the weight, unless otherwise indicated. The 4,4'-diphenylmethane diisocyanate which is used as starting material in the following examples is a technical product containing 99,0% by weight of the 4,4'-isomer.

EXAMPLES

Example 1 — Production of a polyisocyanate mixture 74 g of n-butanol was slowly added to 1000 g of molten 4,4'-diphenylmethane diisocyanate (NCO/OH ratio 8:1) at a temperature of 60° C. and stirring was carried out at this temperature until the NCO content of 27.4% calculated for urethane formation was reached. 0.1 g of zinc acetylacetonate was then added and the temperature was increased to 100° C. Stirring was carried out at this temperature until the NCO content of 23.5% calculated for allophanate formation was reached. The reaction was then terminated by adding 0.1 g of benzoyl chloride. A liquid, pale yellow colored polyisocyanate mixture with a viscosity of 300 mPa.s (23° C.) was obtained. The product was non-crystallizing at a temperature of 5° C. over a storage period of several weeks. When stored at 0° C. the product becomes turbid after approximately 5 days. The calculated allophanate group content of the product was 9.4%. The $C^{13}$-NMR spectrum only showed signals at 156 ppm and 151.5 ppm in the carbonyl range (corresponding to allophanate structures) and 120 ppm (corresponding to isocyanate structures).

Example 2 — Production of a polyisocyanate mixture

In accordance with the procedure set forth in example 1, 875 g of 4,4'-diphenyl-methane diisocyanate were reacted with 74 g of n-butanol (NCO/OH ratio 7:1). The polyisocyanate mixture obtained had a viscosity of 1100 mPa.s (23° C.) and an NCO content of 22.0%. The product was non-crystallizing at a temperature of 0° C. over a storage period of several weeks. The calculated allophanate group content of the product was 10.6%.

Example 3 — Production of a polyisocyanate mixture

In accordance with the procedure set forth in example 1, 750 g of 4,4'-diphenylmethane diisocyanate were reacted with 74 g of n-butanol (NCO/OH ratio 6:1). The polyisocyanate mixture obtained had a viscosity of 5000 mPa.s (23° C.) and an NCO content of 20.2%. The product was non-crystallizing at a temperature of 0° C. over a storage period of several weeks. The calculated allophanate group content of the product was 2.2%.

Example 4 — Production of a polyisocyanate mixture

In accordance with procedure set forth in example 1, 812 g of 4,4'-diphenyl-methane diisocyanate were reacted with 66.6 g of n-butanol mixed with 15.8 g of 1-decanol (NCO/OH ratio 6.5:1). The polyisocyanate mixture obtained had a viscosity of 1800 mPa.s (23° C.) and an NCO content of 21.1%. The product was non-crystallizing at a temperature of 0° C. over a storage period of several weeks. The calculated allophanate group content of the product was 11.3%.

Example 5 — Production of a polyisocyanate mixture

In accordance with procedure set forth in example 1, 875 g of 4,4'-diphenylmethane diisocyanate were reacted with 102 g of n-hexanol (NCO/OH ratio 7:1). The polyisocyanate mixture obtained had a viscosity of 680 mPa.s (23° C.) and an NCO content of 21.4%. The product was non-crystallizing at a temperature of 0° C. over a storage period of several weeks. The calculated allophanate group content of the product was 10.3%.

Example 6 — Production of a solvent-free two-component polyurethane coating composition 180 g of the polyisocyanate mixture from example 1 was intimately mixed with 350 g of a commercial polyol based on castor oil (Desmophen 1150, a product from Bayer AG). The processing time of the mixture was 45 minutes. A film cast onto a sheet of glass dried to a bubble-free, hard, tough, high-gloss, abrasion-resistant coating. After storage for 7 days at ambient temperature, a Shore D hardness of 70 was measured on a cast test piece.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate mixture which is a reaction product of 4,4'-diphenylmethane diisocyanate, is a liquid a 5° C. and above and has
   A) an NCO content of 14.5 to 24% by weight and
   B) an allophanate group content (calculated as $C_2HN_2O_3$ molecular weight=101) of 7.7 to 14.5 % by weight and
   C) said reaction product is prepared by reacting
      a) 4,4'-diphenylmethane diisocyanate with
      b) one or more monohydric alcohols having 4 to 16 carbon atoms per molecule,
   at an NCO/OH equivalent ratio of 5:1 to 8.5:1 to form urethane groups and subsequently allophanate groups.

2. The polyisocyanate mixture of claim 1 wherein said monohydric alcohols are linear, monohydric alcohols having 4 to 10 carbon atoms.

3. A process for the production of a polyisocyanate mixtures which is liquid at temperatures of over 5° C. and above by reacting 4,4'-diphenylmethane diisocyanate with one or more monohydric alcohols having 4 to 16 carbon atoms at an NCO/OH equivalent ratio of 5:1 to 8.5:1 and at a temperature of up to 160° C. to form urethane groups and during or subsequent to urethane formation, converting the urethane groups to allophanate groups in the presence of a catalyst which promotes allophanate formation.

4. The process of claim 3 wherein said catalyst is selected from one or more metal compounds from groups IIIa, IVa, Ib, IIb, VIb VIIb or VIIIb of the periodic chart of elements, which are soluble in the reaction mixture.

5. The process of claim 3, wherein said catalyst is tin(II) octoate or zinc acetylacetonate.

6. A two-component polyurethane coating composition comprising the polyisocyanate mixture of claim 1 and a polyhydroxyl compound.

* * * * *